United States Patent
Lyle et al.

[11] Patent Number: 5,898,101
[45] Date of Patent: Apr. 27, 1999

[54] METHOD OF OPERATING CHEMICAL SENSORS

[75] Inventors: Robert P. Lyle, Chandler; Henry G. Hughes, Scottsdale, both of Ariz.

[73] Assignee: Motorola, Inc., Schaumburg, Ill.

[21] Appl. No.: 08/979,353

[22] Filed: Nov. 26, 1997

Related U.S. Application Data

[63] Continuation of application No. 08/508,201, Jul. 27, 1995, abandoned.

[51] Int. Cl.⁶ .................................................. G01N 27/12
[52] U.S. Cl. .......................... 73/23.2; 73/23.2; 73/31.06
[58] Field of Search ................................ 73/23.2, 23.31, 73/23.34, 31.01, 31.02, 31.03, 31.05, 31.06; 422/83, 90, 94, 95

[56] References Cited

U.S. PATENT DOCUMENTS

| | | | |
|---|---|---|---|
| 4,567,475 | 1/1986 | Bukowiecki et al. | 73/31.06 X |
| 4,627,269 | 12/1986 | Forster et al. | 73/31.06 |
| 4,847,783 | 7/1989 | Grace et al. | 364/497 |
| 4,984,446 | 1/1991 | Yagawara et al. | 73/31.06 |
| 5,055,266 | 10/1991 | Stetter et al. | 422/83 |
| 5,055,268 | 10/1991 | Martin | 422/84 |
| 5,151,166 | 9/1992 | Harral et al. | 204/425 |
| 5,517,182 | 5/1996 | Yasunaga | 73/31.06 X |
| 5,551,283 | 9/1996 | Manaka et al. | 73/31.01 |

*Primary Examiner*—Michael Brock
*Attorney, Agent, or Firm*—George C. Chen; Joe E. Barbee

[57] ABSTRACT

A method of operating chemical sensors (21) uses synchronously pulsed signals to reduce the power consumption of the chemical sensors (21). A first voltage source can be used to control and to heat multiple heating elements of the chemical sensors (21). The first voltage source can also be used to control other sensors which do not require elevated temperature operation. A second voltage source can be used to operate and bias the chemical sensors (21) heated by the multiple heating elements. Power consumption is reduced by turning or pulsing off the heating element (16) when it is not used.

15 Claims, 2 Drawing Sheets

METHOD OF OPERATING CHEMICAL SENSORS

This application is a continuation of prior application Ser. No. 08/508,201, filed Jul. 27, 1996, now abandoned.

BACKGROUND OF THE INVENTION

This invention relates, in general, to a method of operating chemical sensors, and more particularly, to a method of operating chemical sensors which reduces power consumption.

Chemical sensors are used to monitor dangerous and other toxic gases including carbon monoxide, methane, hydrogen, automobile exhaust, and biomedical and industrial emissions. Generally using an ac power source, chemical sensors need to have a backup power supply, such as a battery, which should last for several days to ensure reliability of the chemical sensor system Moreover, with the constantly growing need for more portable systems and remotely controlled systems, many chemical sensors need to rely entirely on battery powered operation. However, current methods of operating metal oxide based chemical sensors consume large quantities of power which drastically shorten battery life and, therefore, are not suited for portable applications or battery powered backup operations.

Previous attempts have been made to reduce power consumption by, among other methods, altering the size and composition of chemical sensors, adding heat reflectors and thermal insulators to the chemical sensors, and pulsing a single heater of a single sensor element. However, none of the prior schemes for a low power consumption system have significantly extended battery life to a practical or efficient level Alternative technologies including optically based sensors are currently battery powered but are compatible with neither low cost silicon fabrication nor integration schemes.

Existing gas monitoring schemes do not compensate for varying environmental factors. For instance, temperature and humidity fluctuations can detrimentally affect the accuracy of chemical sensors. Therefore, environmental calibration is a necessary feature for reliable and precise chemical sensors.

Furthermore, redundancy in gas detection is a desirable feature to further improve the reliability and safety of chemical sensors.

Accordingly, a need exists for a method of operating chemical sensors which is compatible with battery powered operation for backup, portable, and remotely controlled applications. The method should increase battery life up to a pragmatic level, should maintain a safe and reliable detection scheme, and should not be expensive. The method should permit environmental calibration and should also incorporate gas sensing redundancy.

DETAILED DESCRIPTION OF THE DRAWINGS

Figure 1:
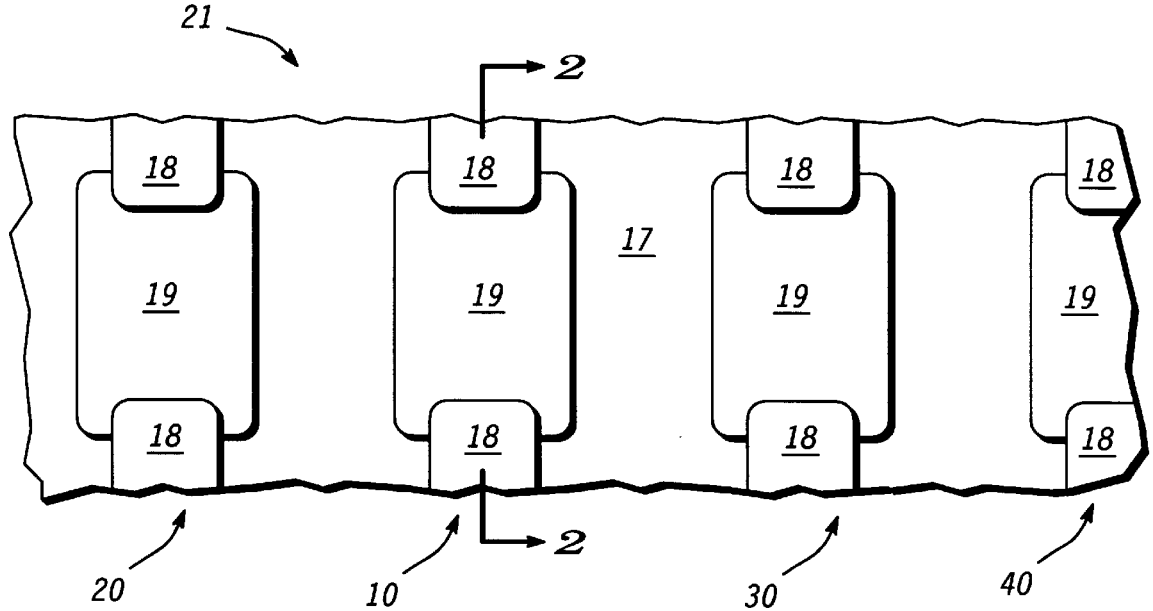
FIG. 1 illustrates a partial top view of a semiconductor substrate having a plurality of chemical sensors in accordance with the present invention.

Turning to FIG. 1 for a more detailed description of the subject invention, FIG. 1 illustrates a partial top view of semiconductor substrate or substrate 12 having a plurality of chemical sensors 21. Plurality of chemical sensors 21 or chemical sensors 10, 20, 30, and 40 portray chemical sensors which are known in the art. Chemical sensors 10, 20, 30, and 40 can be located on a common substrate as depicted in FIG. 1 or can be located on separate substrates.

Figure 2:
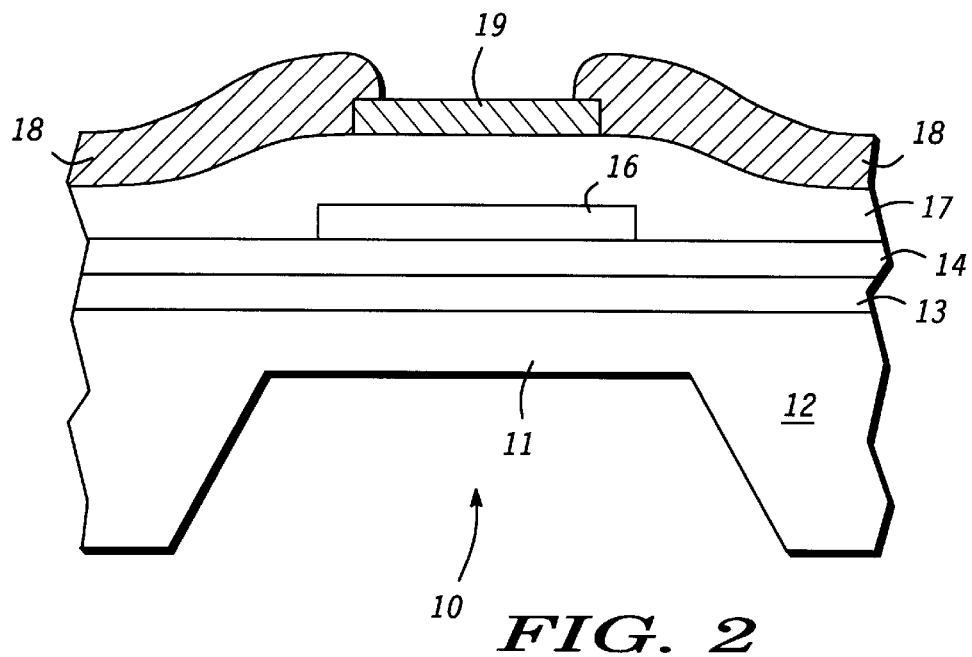
FIG. 2 depicts a partial cross-sectional view of a conventional metal oxide based chemical sensor.

A partial cross-sectional view of a conventional metal oxide based chemical sensor, such as chemical sensor 10, is depicted in FIG. 2. Referring to FIGS. 1 and 2, chemical sensor 10 comprises substrate 12 supporting layer 13 of silicon dioxide and heating element 16 which is surrounded by layers 17 and 14 of silicon dioxide or, preferably, silicon-nitride. Signal line or metal layer 18 provides electrical coupling from an excitation source, voltage source, current source, or other signal source (not shown) to sensing element or sensing portion 19 of chemical sensor 10. Circuitry for the signal source can be on a separate chip or can be fabricated in substrate 12 for an integrated chemical sensor system. An additional signal source (not shown) is electrically coupled to heating element 16 to bias heating element 16 to an appropriate temperature.

Substrate 12 comprises semiconducting materials including silicon, silicon germanium, gallium arsenide, indium phosphide, or the like. Substrate 12 is thinned to form portion or membrane 11 in order to decrease the thermal mass of substrate 12 around the area of heating element 16. Membrane 11 can be chemically etched or physically micromachined. Heating element 16 comprises silicon (i.e. :polysilicon), other doped and undoped materials, or metals (i.e. :platinum) which transfer heat quickly and efficiently. Layers 13, 14, and 17 can also consist entirely of a single type of dielectric or insulator. The purpose of layers 13, 14, and 17 is to provide electrical, but not thermal, insulation or isolation between metal layer 18, sensing portion 19, and substrate 12.

It is noted that the heating element or heating elements of a chemical sensor system can be located on a separate substrate from the substrate having the chemical sensors. However, for efficient heating and space conservation, it is desirable for the heater and the chemical sensor to be located on the same substrate as shown in FIG. 2.

Metal layer 18 comprises chromium, titanium, and platinum or other conducting schemes compatible with sensing portion 19. Sensing portion 19 comprises tin oxide, titanium oxide, gold, zinc oxide or other appropriate materials dependent upon a desired gas to be monitored. Sensing portion 19 can be doped to enhance the sensitivity and selectivity of chemical sensor 10. Suitable dopants include, but are not limited to, antimony, tin, and gadolinium. Sensing portion 19 can also comprise an overlying catalyst layer such as palladium, platinum, tin, or the like.

As known in the art, sensing portion 19 comprises materials whose resistance changes upon exposure to a gas of interest. When the gas of interest is present, sensing portion 19 acts as a catalyst to a reaction resulting in a resistance change in sensing portion 19. The initial resistivity of sensing portion 19 is typically between approximately 10 k$\Omega$ and approximately 50 M$\Omega$ at elevated temperatures. Different combinations of the composition, doping level, and catalyst layer of sensing portion 19 and the bias temperature of heating element 16 permit sensing of different types of gases.

Chemical sensor 10 is heated by heating element 16 to catalyze the chemical reaction between sensing portion 19 and the desired gas. An example of such a chemical reaction is described below. Assume sensing portion 19 comprises tin oxide to monitor the presence of carbon monoxide. In this case, sensing portion 19 can be n-type material and have free electrons. However, oxygen from an ambient atmosphere can be adsorbed onto the exposed surface of the tin oxide which increases the resistance of the tin oxide or sensing portion 19. The increased resistance results from the free electrons of the tin oxide being used to form the bonds between the oxygen and the tin oxide. When carbon monoxide is introduced into the ambient atmosphere, the carbon monoxide can be oxidized by the oxygen on the tin oxide to form carbon dioxide. Because the formation of carbon dioxide removes oxygen from the tin oxide or sensing portion 19, the free electrons are no longer used to form bonds, and thus, the resistance of sensing portion 19 is lowered. When the carbon monoxide is no longer present in the ambient atmosphere, an oxide layer reforms on the exposed surface of the tin oxide, and the resistance of sensing portion 19 is increased back to its original level.

As known in the art, the control circuit or control circuitry (not shown) detects the change in resistivity of sensing portion 19 by first measuring a current or voltage drop through a known load resistor connected in series with the chemical sensor and then back calculating the voltage drop through sensing portion 19 of chemical sensor. In doing so, the presence of the gas is transformed from a chemical reaction into an electrical signal. The control circuitry can be located on a separate chip or can be fabricated in substrate 12 for an integrated chemical sensor system.

Figure 3:
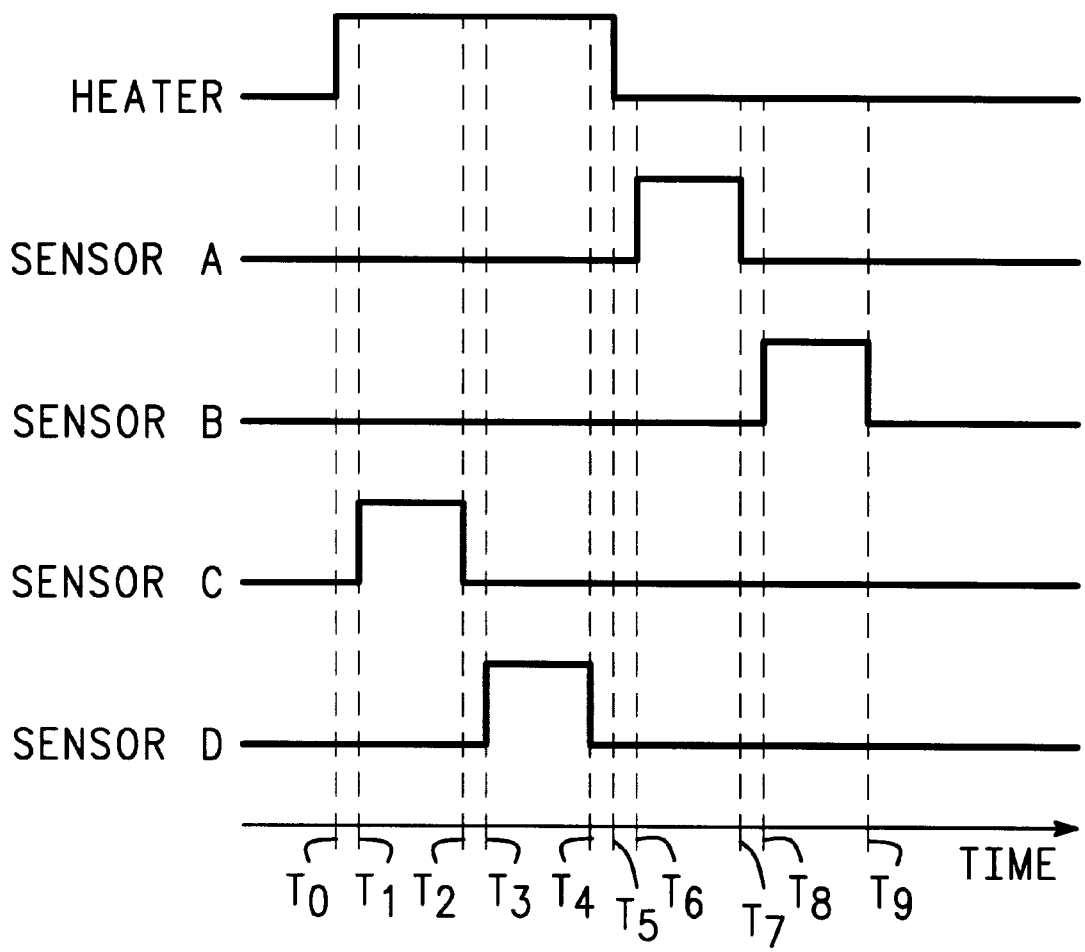
FIG. 3 portrays a synchronized timing diagram of the operation of a plurality of chemical sensors.

FIG. 3 portrays a synchronized timing diagram of the operation of a plurality of chemical sensors in accordance with the present invention. FIG. 3 depicts the timing operation of sensors A, B, C, and D and a heating element identified as "heater". The heater is thermally coupled to sensors A and B. A first voltage source is electrically coupled in parallel to the heater and sensors A and B, and a second voltage source is electrically coupled in parallel to sensors C and D. Time is indicated by the bottom line and increases in a horizontal direction from left to right.

In conventional chemical sensor systems, a dc voltage source of approximately 5 volts is used to continuously heat a heating element which dissipates a large amount of power greater than 100 mW. In the present invention as indicated by the heater line of FIG. 3, heating element 16 is operated in a pulsed mode or fashion by an ac voltage source or other excitation, current, or signal source to dissipate a much smaller amount of power on the order of 10 $\mu$W to 1 mW. However, even a reduction to below 50 mW of power would be a significant improvement over conventional systems. Heating element 16 is turned on or energized at time t0 and turned off at time t5. The pulse amplitude of the heater signal can range from approximately 3 to 7 volts depending upon the desired temperature. A higher voltage produces a higher temperature, and a lower voltage produces a lower temperature for the heating element.

While the first voltage source biases the heating element in an "on state" from time t0 to time t5, sensor C is biased in an "on state" with a different signal from a second voltage source at time t1. The biasing signal can vary from approximately 3 volts to 5 volts in amplitude but is preferably about 5 volts in magnitude. The delay between time t0 and t1 exists to permit the heating element enough time to ramp up to a desired temperature between 300° C. and 500° C. The delay between times t0 and t1 also ensures that when sensor C is turned on and used to monitor or detect a gas that the sensing element of sensor C is elevated to the proper temperature. Usually, a few milliseconds is sufficient to permit the heating element and the sensing element of a chemical sensor to rise to the appropriate temperature. Because the delay is very short, the delta between t0 and t1 can be essentially zero seconds in an alternative embodiment of the present invention.

Creating a pareto chart or itemizing the factors which consume power in a chemical sensor, one will find that the heating element is, by far, the largest contributor of power consumption. While the sensing element consumes very little power ($\mu$A) compared to the heating element (mA) in a steady state condition, power consumption will still be reduced if the bias applied to the sensing element is also pulsed. Furthermore, if a bias is applied only to the chemical sensor under use, several chemical sensors can be controlled by a single voltage source. Consequently, the bias signal from the second voltage source to sensor C is changed to turn sensor C off as shown in FIG. 3 at time t2. The delta between times t1 and t2 can be a few milliseconds. In order to conserve power, sensor C is unbiased after the control circuitry determines the resistance value of the sensing portion of sensor C.

After turning sensor C off at time t2, the second voltage source can be used to turn on sensor D at time t3. If the switching speed of the control circuitry is fast enough, the delay between times t2 and t3 can be essentially zero seconds.

Sensor D can be an identical copy of sensor C and can be used to detect the same gas as sensor C to provide redundancy for the sensor system and to improve the sensor system's reliability. Alternatively, sensor D can be different from sensor C to detect a different gas. Similar to sensor C, sensor D can be turned off at time t4 after the control circuitry has had sufficient time to discern a change, or lack thereof, in resistance of the sensing portion of sensor D. The time required for such an operation is generally a few milliseconds from time t3.

It is important to note that while sensor D is on, the heater is also on. However, after sensor D is unbiased or turned off at time t4, the heater is no longer needed and can be turned off or pulsed off at time t5 to conserve power. Provided that the heater stays on while sensor D is being used to monitor or sense a gas, the delay between times t4 and t5 can be essentially zero seconds.

After the heater is turned off at time t5, FIG. 3 illustrates that the first voltage source can be used to control an additional sensor or additional sensors, namely sensors A and B. Sensor A is pulsed on at time t6 by the first voltage source. Again, the delay between times t5 and t6 can be essentially zero in an alternative embodiment. When sensor A is biased in an off state at time t7, sensor B is then turned on by pulsing a different signal from the first voltage source at time t8 and subsequently turned off by yet another signal from the first voltage source at time t9. The delays between times t6 and t7 and between times t8 and t9 are similar to the delays between times t1 and t2 and between times t3 and t4 for similar reasons described above. Furthermore, the delay between times t7 and t8 is similar to the delay between times t2 and t3 for similar reasons mentioned previously.

Since sensors A and B are operated independently when the heater is off, sensors A and B will be operated at room temperature and, therefore, can be a humidity sensor, a temperature sensor, or a pressure sensor. Accordingly, sensors A and B, can be used to calibrate a sensor system according to fluctuating or varying environmental conditions and to increase the accuracy and precision of the chemical sensor system.

FIG. 3 illustrates a single cycle of synchronized operation for a chemical sensor system. After time t9, the previously described operation of the heater and sensors A, B, C, and D is duplicated. In other words, the steps from time t0 through t9 are sequentially repeated over and over again. A delay between the end of one cycle and the beginning of another cycle may be inserted into the synchronized operation if desired. However, if a delay prior to the repetition of the cycle is used, the delay should not be too large such that it may jeopardize safety considerations.

In summary of the above description of FIG. 3, a first voltage source is used to independently control the heater, sensor A, and sensor B while a second voltage source is used to independently control sensor C and sensor D. The main source of power dissipation, the heater, is pulsed to an "on state" when needed and is otherwise left in an "off state". The chemical sensor system described above is safe and reliable because it permits the continuous detection and monitoring of different gases or of the same gas, the latter of which provides redundancy and improves reliability.

The operation of the chemical sensors of FIG. 3, or more specifically, the duty cycle of a single bias pulse (i.e. :from time t1 to time t2 of FIG. 3) can be shortened to permit additional chemical sensors (i.e. :sensors E, F, G, H, etc. ) to be used in the system without lengthening the period of a single cycle. The time between times t1 and t2 can be shortened provided that a sufficient time still remains for the control circuitry to determine whether or not an alteration in the resistance of the sensing portion has occurred. As mentioned previously, the fabrication and operation of silicon based chemical sensors is inexpensive, especially compared to optically based systems.

One skilled in the art will understand that the operation scheme in FIG. 3 powers on the heater for approximately half of the cycle from time t0 through t9 or approximately half of the time that sensors A, B, C, and D are in operation. Consequently, the power consumption is essentially reduced in half since the biasing of sensors A, B, C, and D consume very little power relative to the heater. It is important to note that further reductions in power consumption can also be realized by employing a multitude of variations of the method illustrated in FIG. 3.

A few of those variations are described below. For example, a system having multiple chemical sensors can comprise a first heater thermally coupled to a first one of the chemical sensors and a second heater thermally coupled to a second one of the chemical sensors, wherein the first heater and the first chemical sensor are thermally isolated from the second heater and the second chemical sensor and vice versa. The two heaters connected such that they can be consecutively and synchronously biased to the same or different temperatures from the same voltage source. In this manner, the first and second chemical sensors can detect the same gas, or the first and second chemical sensors can detect a first gas and a second gas, respectively. In this manner, a single ac voltage source can be used to independently operate multiple heating elements, and thus, power dissipation is reduced compared to conventional systems which utilize a separate dc voltage source for each heating element of the system.

Alternatively, the heater of FIG. 3 can be biased with a different voltage from the first voltage source after time t3 and before time t4 to heat or elevate sensor D to a different or second temperature. The heater can be converted to an off state before being pulsed or raised to the different temperature, or the heater can be pulsed from the first temperature directly to the second temperature. Additionally, sensors A and C can be powered by the same voltage source as sensors C and D instead of being powered by the same voltage source as the heater.

Furthermore, in a multiple sensor system, one of the sensors can be a reference sensor as known in the art. In a chemical sensor system with a plurality of chemical sensors, the chemical sensors can be located on separate chips or, preferably, can be located on the same semiconductor chip with the control circuitry and the voltage sources to create an integrated chemical sensor system. Yet another embodiment has a chemical sensor system comprising a single chemical sensor with a single heating element.

Therefore, in accordance with the present invention, it is apparent there has been provided an improved method of operating chemical sensors which overcomes the disadvantages of the prior art. The present invention eliminates excessive power consumption, compensates for environmental variations, is not expensive, provides redundancy for gas monitoring, and is safe and reliable.

We claim:

1. A method of operating a chemical sensor system, the method comprising:
    (a) providing a first excitation source and a second excitation source;
    (b) providing chemical sensors electrically coupled to the first excitation source;
    (c) providing a first heating element electrically coupled to the second excitation source;
    (d) biasing the first heating element to a first temperature with the second excitation source;
    (e) biasing a first one of the chemical sensors with the first excitation source, the first one of the chemical sensors being heated by the first heating element to detect a first gas;
    (f) unbiasing the first one of the chemical sensors;
    (g) unbiasing the first heating element; and
    (h) sequentially repeating steps (d) through (g) prior to turning off the chemical sensor system.

2. The method according to claim 1, further providing a semiconductor substrate having the first and second excitation sources, the chemical sensors, and the first heating element.

3. The method according to claim 1, further comprising:
    (i) biasing a second one of the chemical sensors with the first excitation source; and
    (j) unbiasing the second one of the chemical sensors,
    wherein steps (i) and (j) occur after step (f) and before step (g), wherein the second one of the chemical sensors is heated by the first heating element, and wherein step (h) further comprises consecutively repeating steps (d), (e), (f), (i), (j), and (g).

4. The method according to claim 3, further comprising detecting the first gas with the second one of the chemical sensors.

5. The method according to claim 3, further comprising detecting a second gas with the second one of the chemical sensors.

6. The method according to claim 1, further comprising:
    (i) providing a second heating element electrically coupled to the second excitation source;
    (j) biasing the second heating element with the second excitation source to a second temperature;
    (k) biasing a second one of the chemical sensors with the first excitation source, the second one of the chemical sensors heated by the second heating element;

(l) unbiasing the second one of the chemical sensors; and (m) unbiasing the second heating element, wherein steps (i) through (m) occur after step (g) and before step (h) and wherein step (h) further comprises consecutively repeating steps (d) through (g) and (i) through (m).

7. The method according to claim 6, wherein only one of the chemical sensors is biased at a time by the first excitation source.

8. The method according to claim 1, further providing a semiconductor substrate having the first and second excitation sources, the chemical sensors, the first heating element, and a control circuit for controlling repetition of steps (d) through (g).

9. The method according to claim 1, further comprising:

(i) biasing the first heating element to a second temperature with the second excitation source;

(j) biasing a second one of the chemical sensors with the first excitation source, the second one of the chemical sensors heated by the first heating element;

(k) unbiasing the second one of the chemical sensors; and (l) unbiasing the first heating element, wherein steps (i) through (l) occur after step (g) and before step (h) and wherein step (h) further comprises consecutively repeating steps (d) through (g) and (i) through (l).

10. The method according to claim 1, wherein only one of the chemical sensors is biased at a time by the first excitation source.

11. A method of operating chemical sensors, the method comprising:

(a) providing a first excitation source and a second excitation source;

(b) providing chemical sensors electrically coupled to the first excitation source;

(c) providing a first heating element electrically coupled to the second excitation source;

(d) biasing the first heating element to a first temperature with the second excitation source;

(e) biasing a first one of the chemical sensors with the first excitation source, the first one of the chemical sensors being heated by the first heating element to detect a first gas;

(f) unbiasing the first one of the chemical sensors;

(g) unbiasing the first heating element;

(h) providing an additional sensor electrically coupled to the second excitation source;

(i) biasing the additional sensor with the second excitation source;

(j) unbiasing the additional sensor; and (k) consecutively repeating steps (d) through (k).

12. The method according to claim 11, further providing a temperature sensor for the additional sensor.

13. The method according to claim 11, further providing a humidity sensor for the additional sensor.

14. The method according to claim 11, further providing a pressure sensor for the additional sensor.

15. The method according to claim 11, further providing a semiconductor substrate having the first and second excitation sources, the chemical sensors, the first heating element, and the additional sensor.

* * * * *